(12) United States Patent
Robbins et al.

(10) Patent No.: US 11,510,711 B1
(45) Date of Patent: Nov. 29, 2022

(54) PEDICLE SCREW SYSTEM AND METHOD

(71) Applicant: Alevio, LLC, Birmingham, AL (US)

(72) Inventors: Joseph Robbins, Vestavia Hills, AL (US); Howard Moore, Round Rock, TX (US)

(73) Assignee: ALEVIO, LLC, Birmingham, AL (US)

( * ) Notice: Subject to any disclaimer, the term of this patent is extended or adjusted under 35 U.S.C. 154(b) by 0 days.

(21) Appl. No.: 17/397,983

(22) Filed: Aug. 9, 2021

(51) Int. Cl.
*A61B 17/70* (2006.01)
*A61B 17/86* (2006.01)

(52) U.S. Cl.
CPC ...... *A61B 17/7082* (2013.01); *A61B 17/7032* (2013.01); *A61B 17/8685* (2013.01)

(58) Field of Classification Search
CPC ............ A61B 17/7032; A61B 17/7034; A61B 17/7035; A61B 17/7037; A61B 17/7076; A61B 17/7077; A61B 17/708
USPC ....... 606/264–267, 269, 272, 273, 277, 278, 606/305, 308, 319, 328
See application file for complete search history.

(56) References Cited

U.S. PATENT DOCUMENTS

| | | | | |
|---|---|---|---|---|
| 10,070,897 B1* | 9/2018 | Gregory | ............. | A61B 17/7032 |
| 10,258,385 B1* | 4/2019 | Doubler | ............. | A61B 17/7037 |
| 11,202,661 B1* | 12/2021 | Rezach | ............. | A61B 17/7086 |
| 2005/0131408 A1* | 6/2005 | Sicvol | ................ | A61B 17/7032 606/301 |
| 2009/0105756 A1* | 4/2009 | Richelsoph | ........ | A61B 17/7035 606/301 |
| 2018/0353213 A1* | 12/2018 | Biedermann | ...... | A61B 17/7001 |
| 2019/0117270 A1* | 4/2019 | Biedermann | ...... | A61B 17/8605 |

* cited by examiner

*Primary Examiner* — Eduardo C Robert
*Assistant Examiner* — David C Comstock
(74) *Attorney, Agent, or Firm* — C. Brandon Browning; Maynard, Cooper & Gale, PC

(57) ABSTRACT

A pedicle screw system and methods of using same, the system including a pedicle screw with a screw head and a rod support housing with a head capture opening surrounded by relief slots. The rod support housing has an interior gripping ridge and an exterior locking groove. Pressing the screw head into the head capture opening results in regions of the rod support housing between the relief slots flexing outwardly to allow the screw head to pass over the gripping ridge, and the regions to cease flexing outwardly after the screw head is seated within the rod support housing. Pressing a locking ring over the head capture opening causes regions of the rod support housing between the relief slots to flex inwardly and allow a locking tab of the locking ring to pass into the locking groove, after which the regions cease flexing inwardly.

20 Claims, 6 Drawing Sheets

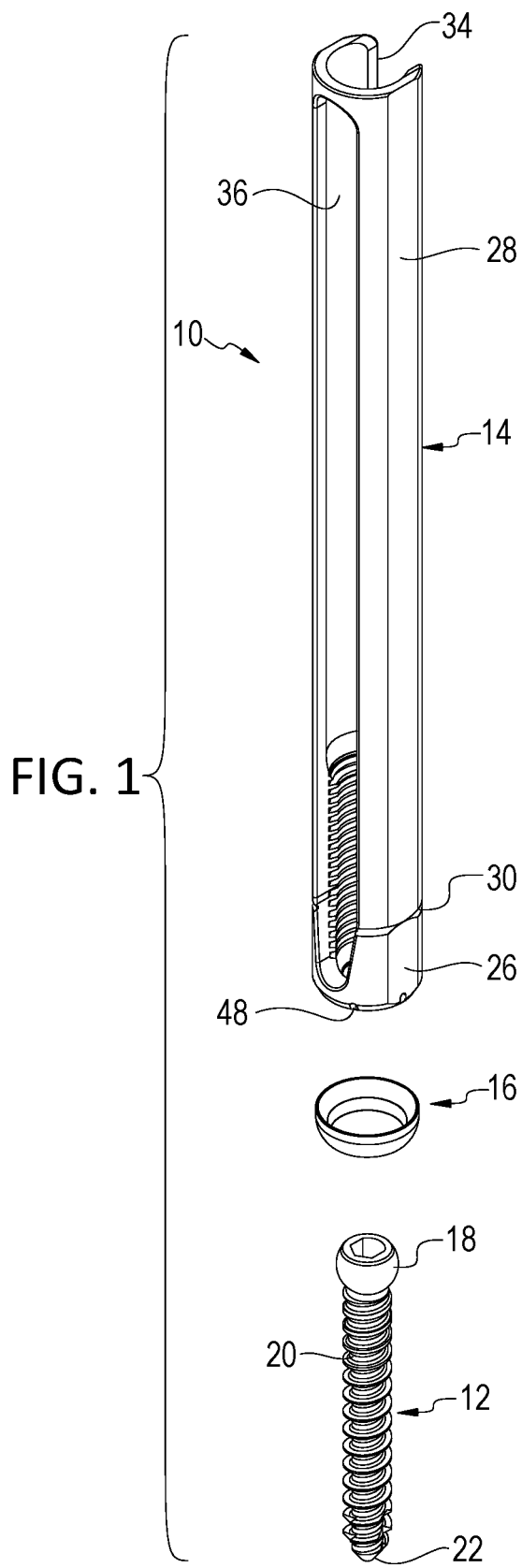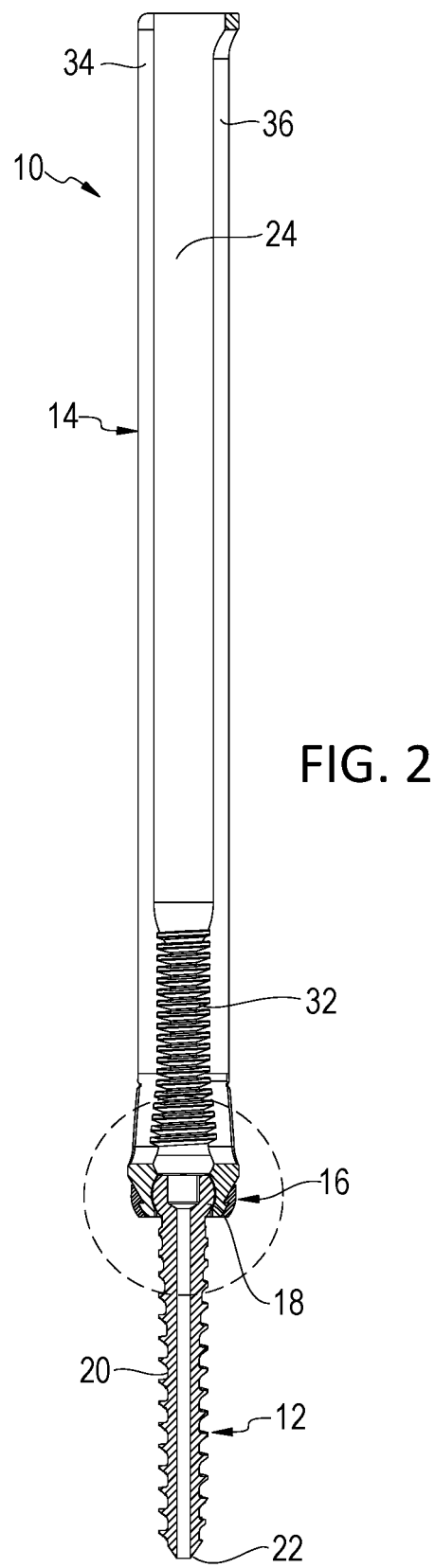

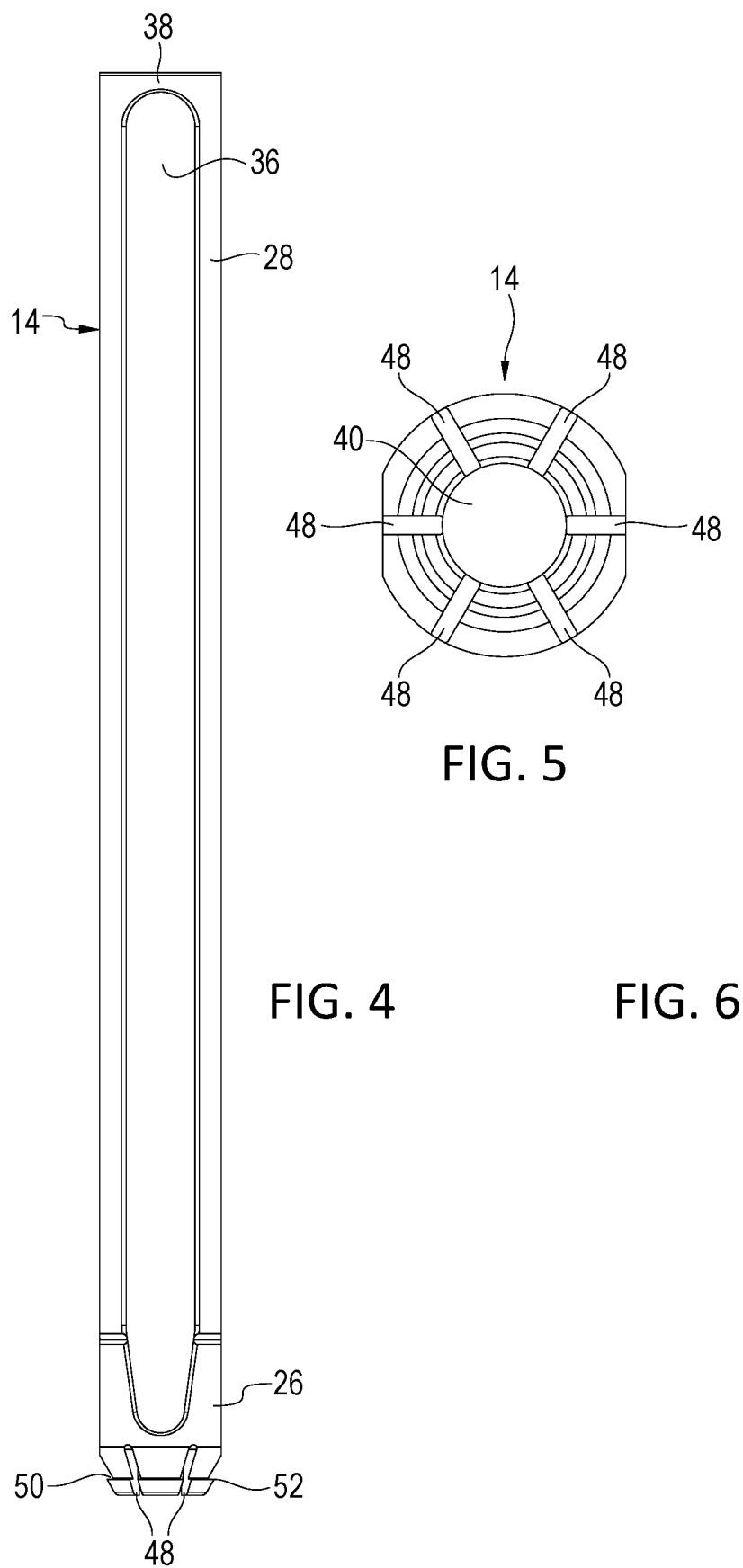

PEDICLE SCREW SYSTEM AND METHOD

TECHNICAL FIELD

The present invention is directed to a pedicle screw system and method. More particularly, the present invention is directed to a pedicle screw system configured for insertion into a pedicle of a vertebra and methods of assembling and using same for immobilization or fusion of portions of the spine.

BACKGROUND OF INVENTION

Spinal fusion is a surgical technique that may be performed when the spine is injured or otherwise damaged as a result of, for instance, degenerative disc disease. Trauma or diseases affecting the spine can lead to pressure and pain, which spinal fusion aims to alleviate or reduce by restricting movement and adding stability. The surgical procedure generally involves the decompression of the spine, placement of hardware, including pedicle screws and connecting rods, and the insertion of bone graft material, resulting in the fusion of two or more vertebrae.

Pedicle screws are a type of bone screw that are designed specifically for insertion into the vertebral pedicles. Insertion of pedicle screws is undertaken prior to placement of rods that connect the inserted pedicle screws and provide stability as vertebrae are joined. Procedures to place pedicle screws include steps to identify the correct placement location, insertion angle, and screw dimensions. Placement often begins by providing a channel within a vertebra for pedicle screw placement, where the channel traverses a pedicle and enters a vertebral body of the vertebra without breaching the spinal canal.

Pedicle screws are often inserted using an assembly that includes not only the pedicle screw, but also a tower or extension device through which a driver can operate and rotate the pedicle screw in its intended position. The tower or extension device may then be removed, leaving the inserted pedicle screw and hardware for rod attachment to the head region of the inserted pedicle screw. Rod attachment hardware should be firmly connected to the pedicle screw to provide stability as two or more pedicle screws are connected via rods. However, the rod attachment hardware may be somewhat mobile after connection with the pedicle screw head, so that stress is reduced on the vertebrae during insertion and further pain, pressure, or injury is avoided. Thus, a strong, yet somewhat adjustable or mobile connection is desirable between a pedicle screw and rod attachment housing.

SUMMARY OF THE INVENTION

The present invention is directed to a pedicle screw system and methods of using same for assembly and insertion in vertebral pedicles. The pedicle screw system may include a pedicle screw with a screw head and a screw shaft, where the screw head has a major diameter and is located at a proximal end of the pedicle screw and the screw shaft extends from the screw head to a screw tip at a distal end of the pedicle screw. The pedicle screw system may further include a modular pedicle tower with a rod support housing at a distal end of the pedicle tower, an extension portion at a proximal end of the pedicle tower, a separation notch forming an indention between the rod support housing and the extension portion, and a central channel extending from the proximal end to the distal end of the pedicle tower. The rod support housing may include a head capture opening surrounded circumferentially by relief slots at a distal end of the rod support housing, a gripping ridge along an interior surface of the rod support housing, an inner diameter formed by an innermost point of the gripping ridge that is slightly smaller than the major diameter of the screw head, and a locking groove along an exterior surface of the distal end of the rod support housing with an outer diameter formed by an outermost edge of the locking groove. The pedicle screw system may include a locking ring with a central opening and a locking tab, where the locking tab is located along and extends from an interior surface of the locking ring and where a tab diameter formed by an innermost point of the locking tab is slightly smaller than the outer diameter of the locking groove.

Regions of the rod support housing between the relief slots may be configured to flex outwardly and the rod support housing may be configured to receive the screw head upon pressing the screw head through the head capture opening and over the gripping ridge. Further, regions of the rod support housing between the relief slots may be configured to flex inwardly and the rod support housing may be configured to receive the locking ring upon pressing the locking ring over the head capture opening and engaging the locking tab within the locking groove, such that, when the screw head is seated within the rod support housing and the locking ring is subsequently placed over the rod support housing, regions of the rod support housing between the relief slots are thereafter unable to flex and both the locking ring and the pedicle screw are locked to the rod support housing.

The pedicle screw system may further include a threaded driver region within the central channel and spanning the proximal end of the rod support housing and a distal end of the extension portion, as well as a stopping ridge along the interior surface of the rod support housing configured to prevent the pedicle screw from entering the threaded driver region. The modular pedicle tower may include a cutout and a longitudinal slot, the cutout extending from a connection bridge at the proximal end of the pedicle tower to the distal end of the pedicle tower and the longitudinal slot extending from the proximal end of the pedicle tower to the distal end of the pedicle tower. The extension portion may be configured for separation into at least two panels upon severance of the connection bridge and the extension portion may be further configured for removal from the rod support housing upon bending the at least two panels at the separation notch.

According to another aspect of the invention, there is provided a method of assembling a pedicle screw system. The method may include the step of providing a pedicle screw and a modular pedicle tower, the pedicle screw including a screw shaft and a screw head with a major diameter, and the pedicle tower including a rod support housing and an extension portion, where the rod support housing includes a head capture opening surrounded circumferentially by relief slots at a distal end of the rod support housing, a gripping ridge along an interior surface of the rod support housing, an inner diameter formed by an innermost point of the gripping ridge that is slightly smaller than the major diameter of the screw head, and a locking groove along an exterior surface of the rod support housing with an outer diameter formed by an outermost edge of the locking groove. A further step may include aligning the screw head of the pedicle screw with the head capture opening, where the screw shaft is positioned outside of the head capture opening, and pressing the screw head into the head capture opening such that regions of the rod support housing between the relief slots flex outwardly to allow the screw head to pass over the gripping ridge, and regions of the rod support housing between the relief slots cease to flex outwardly after the screw head is seated within the rod support housing. Yet another step may include placing a locking ring around the screw shaft and against the head capture opening, the locking ring comprising a central opening and a locking tab, where the locking tab is located along and extends from an interior surface of the locking ring and where a tab diameter formed by an innermost point of the locking tab is slightly smaller than the outer diameter of the locking groove. Pressing the locking ring over the head capture opening of the rod support housing may result in regions of the rod support housing between the relief slots flexing inwardly to allow the locking tab of the locking ring to pass over the outermost edge of the locking groove and into the locking groove, and regions of the rod support housing between the relief slots ceasing to flex inwardly after the locking tab is seated within the locking groove, such that the pedicle screw system is assembled and locking ring and the pedicle screw are locked to the rod support housing.

Pressing of the screw head over the gripping ridge may further include rotating the pedicle screw during the pressing. In the method, the outward flexing may increase a diameter of the head capture opening by about 0.022 inches and the inward flexing may decrease the diameter of the head capture opening by about 0.016 inches. After locking the locking ring and the pedicle screw to the rod support housing, movement of the screw head over the gripping ridge may force the locking groove into further contact with the locking tab of the locking ring, such that the locking ring prevents the removal of the pedicle screw from the rod support housing.

According to yet another aspect of the invention, there is provided a modular pedicle tulip. The pedicle tulip may include a pedicle screw with a screw head and a screw shaft, where the screw head has a major diameter and is located at a proximal end of the pedicle screw and the screw shaft extends from the screw head to a screw tip at a distal end of the pedicle screw. The pedicle tulip may further include a rod support housing with a central channel, a head capture opening surrounded circumferentially by relief slots at a distal end of the rod support housing, a gripping ridge along an interior surface of the rod support housing, an inner diameter formed by an innermost point of the gripping ridge that is slightly smaller than the major diameter of the screw head, and a locking groove along an exterior surface of the distal end of the rod support housing with an outer diameter formed by an outermost edge of the locking groove. Another component of the pedicle tulip may be a locking ring with a central opening and a locking tab, where the locking tab is located along and extends from an interior surface of the locking ring and where a tab diameter formed by an innermost point of the locking tab is slightly smaller than the outer diameter of the locking groove.

Regions of the rod support housing between the relief slots may be configured to flex outwardly and the rod support housing may be configured to receive the screw head upon pressing the screw head through the head capture opening and over the gripping ridge. Additionally, regions of the rod support housing between the relief slots may be configured to flex inwardly and the rod support housing may be configured to receive the locking ring upon pressing the locking ring over the head capture opening and engaging the locking tab within the locking groove, such that, when the screw head is seated within the rod support housing and the locking ring is subsequently placed over the rod support housing, regions of the rod support housing between the relief slots are thereafter unable to flex and both the locking ring and the pedicle screw are locked to the rod support housing, forming the assembled modular pedicle tulip.

The locking groove may be configured to move into further contact with the locking tab of the locking ring to prevent removal of the pedicle screw when the screw head of the assembled pedicle tulip moves over the gripping ridge. The modular pedicle tulip may further include a threaded driver region at the proximal end of the central channel of the rod support housing, where the threaded driver region of the central channel is tapered toward the proximal end of the rod support housing. A stopping ridge along the interior surface of the rod support housing may be configured to prevent the pedicle screw from entering the threaded driver region. At least a pair of longitudinal slots extending from the proximal end of rod support housing and may be configured to house rods that connect multiple pedicle tulips.

A further understanding of the nature and advantages of the present invention will be realized by reference to the remaining portions of the specification and the drawings.

BRIEF DESCRIPTION OF DRAWINGS

Pedicle screw systems and methods can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 1 is an exploded perspective view of a pedicle screw system in accordance with a first embodiment of the present invention.

FIG. 2 is a sectional view of the assembled pedicle screw system of FIG. 1.

FIG. 4 is an elevational view of a modular pedicle tower section of the pedicle screw system of FIG. 1.

FIG. 5 is a plan view of the modular pedicle tower of the pedicle screw system of FIG. 1.

FIG. 6 is a sectional view of the modular pedicle tower of the pedicle screw system of FIG.

DESCRIPTION OF PREFERRED EMBODIMENTS

Figure 3:
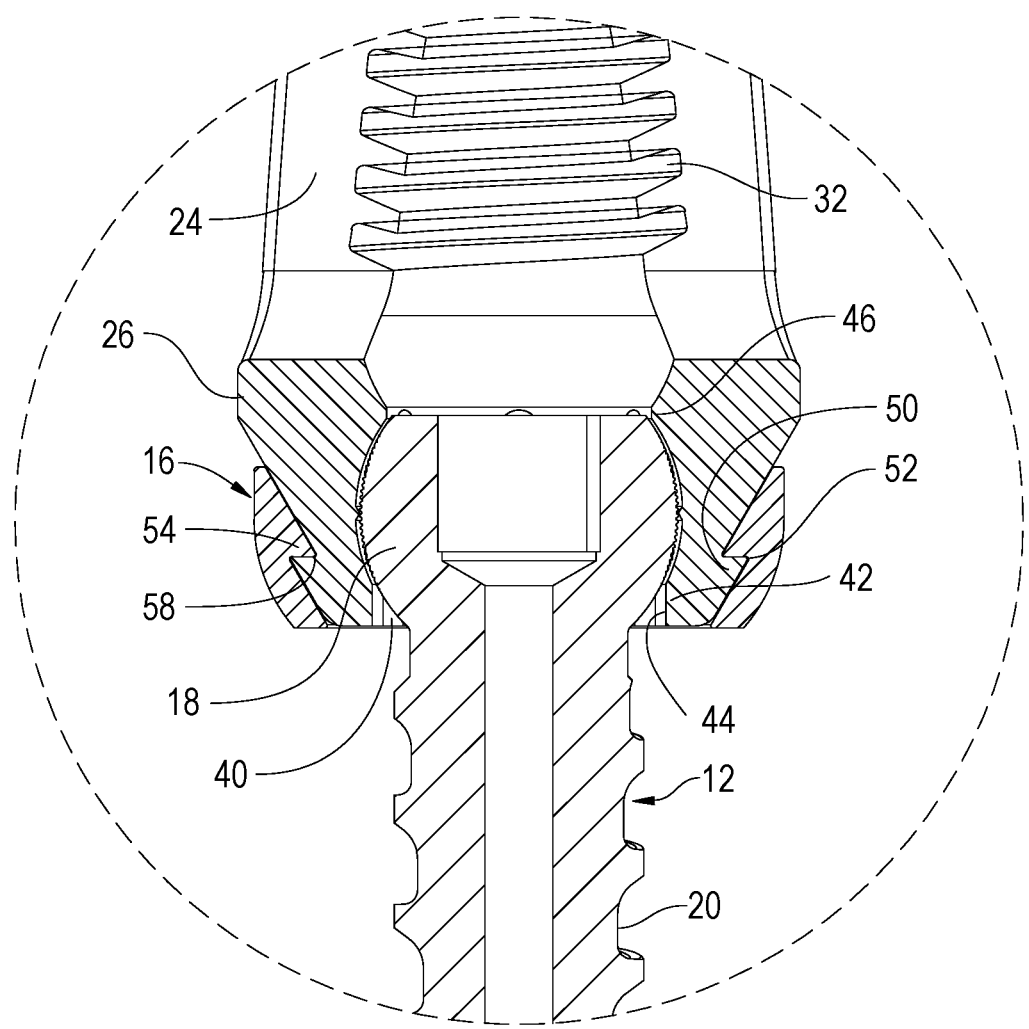
FIG. 3 is a sectional view of a section of the assembled pedicle screw system of FIG. 1 containing a seated and locked pedicle screw.

The present invention is generally directed to pedicle screw systems and methods of using same for assembly prior to and insertion during spinal fusion surgical procedures. Spinal fusion involves inserting the pedicle screw system into a vertebra, traversing the pedicle, and entering the pedicle screw system into the vertebral body. Removal of portions of the pedicle screw system may allow a pedicle tulip to remain in the inserted location, through which rods may be inserted to connect multiple pedicle tulips and stabilize the vertebrae during fusion. FIGS. 1-10 depict an embodiment of a pedicle screw system 10, where like features share like reference numerals. It should be noted that all terms as used herein are given their common meaning as known in the art and as further described and discussed hereafter. As used herein, the singular forms "a", "an", and "the" include plural referents unless the context clearly indicates otherwise.

As used herein, the "interior" location or surface of components or structures is relative to the longitudinal centerline of the central channel or central opening of the pedicle screw system. For instance, an interior surface or wall may be directed toward or face the longitudinal centerline of the central channel or central opening of the pedicle screw system. Similarly, an "innermost point" is a point of a feature or component nearest to and directed toward or facing the longitudinal centerline of the central channel or central opening of the pedicle screw system.

As used herein, the "exterior" location or surface of components or structures is relative to the longitudinal centerline of the central channel or central opening of the pedicle screw system. For instance, an exterior surface or wall may be directed or face away from the longitudinal centerline of the central channel or central opening of the pedicle screw system. Similarly, an "outermost point" is a point of a feature or component farthest from and directed or facing away from the longitudinal centerline of the central channel or central opening of the pedicle screw system.

As used herein, "flexing inwardly" refers to the temporary movement of a component, feature, or portion of a component or feature of the pedicle screw system directed toward the longitudinal centerline of the central channel or central opening of the pedicle screw system.

As used herein, "flexing outwardly" refers to the temporary movement of a component, feature, or portion of a component or feature of the pedicle screw system directed away from the longitudinal centerline of the central channel or central opening of the pedicle screw system.

As used herein, "major diameter" refers to a distance or length measured between two opposing outermost points of a screw head.

Referring to FIG. 1, pedicle screw system 10 is depicted, including a pedicle screw 12, a modular pedicle tower 14, and a locking ring 16. Pedicle screw system 10 has metal components, and generally titanium is used due to its resistance to corrosion and fatigue, compatibility with certain technologies, such as MRI, and ability to permit some temporary displacement due to its elastic modulus. For instance, the Young's modulus of titanium is approximately 110 GPa, and titanium alloys may have a Young's modulus in the range of about 105 to about 120 GPa. Titanium alloys, such as Ti-6Al-4V (titanium with 6% aluminum and 4% vanadium), are regularly used in medical hardware and are compatible with the present invention.

In pedicle screw system 10, pedicle screw 12 includes large major diameter pedicle screws, and dimensions of modular pedicle tower 14 features are adaptable to various pedicle screws 12. In general, pedicle screw 12 includes a screw head 18 at a proximal end of pedicle screw 12 and a screw shaft 20 at a distal end of pedicle screw 12. Screw head 18 has a major diameter and a semi-spherical exterior, with a driver inset at the proximal end of pedicle screw 12 for driver insertion during screw placement. The driver inset is of a shape consistent with the shape of its intended driver, which includes, for example, a hexagon, a Phillips slot, a linear slot, and a square. Various pedicle screws 12 are contemplated for use in pedicle screw system 10, such that pedicle screws 12 have screw head 18 with a major diameter and such that the major diameter of screw head 18 is larger than a diameter of screw shaft 20. Threads of screw shaft 20 may span screw shaft 20 in its entirety, or may be absent in regions as appropriate for intended applications. Screw shaft 20 further terminates at the distal end of pedicle screw 12 in a screw tip 22, which serves as an initiation point for pedicle screw 12 entry into bone or other suitable material at the vertebral insertion location.

Referring to FIGS. 1-2, modular pedicle tower 14 of pedicle screw system 10 includes a central channel 24, a rod support housing 26, an extension portion 28, and a separation notch 30 that separates rod support housing 26 from extension portion 28. Central channel 24 extends longitudinally from a proximal end to a distal end of modular pedicle tower 14 and is partially enclosed by boundaries with an at least partially rounded cross section. In some embodiments not depicted, the cross section of boundaries defining central channel 24 are not be rounded. Central channel 24 includes threaded and unthreaded regions for insertion of a driver. A threaded driver region 32 within central channel 24 spans a proximal end of rod support housing 26 and a distal end of extension portion 28, as shown in FIG. 2. In embodiments not depicted, threaded driver region 32 extends along a greater or lesser length of central channel 24, such that threading is maintained within at least a portion of central channel 24 within rod support housing 26 and separation notch 30. Central channel 24 of modular pedicel tower 14 is exposed from the exterior by openings at the proximal and distal ends of modular pedicle tower 14, as well as by a longitudinal slot 34 and a cutout 36. Longitudinal slot 34 extends from the proximal end of modular pedicle tower 14 to approximately a distal end of threaded driver region 32 of modular pedicle tower 14. Termination of longitudinal slot 34 includes a rounded, squared, pointed, or tapered boundary, or any other termination such that a driver may be inserted and view in central channel 24 and such that extension portion 28 may be removed from rod support housing 26, as detailed further below. Cutout 36 extends from a connection bridge 38 near the proximal end of modular pedicle tower 14 to approximately a distal end of threaded driver region 32 of modular pedicle tower 14. The shape of cutout 36 may be a rounded rectangle, oval, rectangle, or any other shape such that a driver may be inserted and view in central channel 24 and such that extension portion 28 may be removed from rod support housing 26 after connection bridge 38 is severed, as detailed further below. In the example shown in FIGS. 1-6, cutout 36 faces longitudinal slot 34, though cutout 36 may be located in other locations about modular pedicle tower 14 in embodiments that are not depicted.

Referring to FIG. 3, modular pedicle tower 14 includes rod support housing 26 at its distal end, where rod support housing 26 serves to receive screw head 18 of pedicle screw 12. Rod support housing 26 includes a head capture opening 40 at a distal end of rod support housing 26, through which screw head 18 is configured to enter. Head capture opening 40 has a circular cross section, or any cross section similar in shape to that of screw head 18. Additionally, head capture opening 40 serves as the distal opening to central channel 24. Along an interior surface of rod support housing 26, near the distal end of central channel 24, is a gripping ridge 42 with an inner diameter formed by an innermost point 44 of gripping ridge 42 that is slightly smaller than the major diameter of screw head 18. The slightly smaller inner diameter is sufficiently smaller than the major diameter, such that in a resting state without application of pressure, stress, or rotation, screw head 18 does not pass through head capture opening 40 and gripping ridge 42, but also such that with application of pressure, stress, or rotation, head capture opening 40 and gripping ridge 42 are capable of flexing to accommodate the passage of screw head 18. As shown in FIG. 3, the interior surface of rod support housing 26 between head capture opening 40 and gripping ridge 42 is parallel to a longitudinal centerline of central channel 24, while the interior surface of rod support housing 26 between gripping ridge 42 and a stopping ridge 46 is semi-spherical such that screw head 18 may be seated within this region. In embodiments not shown, the interior surface of rod support housing 26 between head capture opening 40 and gripping ridge 42 may be provided at an angle such that the interior surface tapers inward relative to the centerline of central channel 24 from head capture opening 40 to gripping ridge 42. The inner diameter formed by innermost point 44 of gripping ridge 42, though slightly smaller than the major diameter of screw head 18 in its resting state, is configured to be flexible, such that pressure and rotation of pedicle screw 12 during insertion into head capture opening 40 is capable of flexing regions of rod support housing 26 and temporarily enlarging the inner diameter. For example, the outward flexing of regions of rod support housing 26 increases a diameter of head capture opening 40 by about 0.022 inches to accommodate the passage of screw head 18 in one instance. Stopping ridge 46 is shown in FIG. 3 along the interior surface of rod support housing 26 and is configured to prevent pedicle screw 12 from entering threaded driver region 32. A diameter formed at an innermost point of stopping ridge 46 is smaller than a proximal end diameter of screw head 18 and is not capable of flexing to accommodate the passage of screw head 18.

Referring to FIGS. 4-6, head capture opening 40 is surrounded circumferentially by relief slots 48 at a distal end of rod support housing 26. These relief slots 48 extend from head capture opening 40 into rod support housing 26 and terminate prior to reaching the distal end of threaded driver region 32. Termination of relief slots 48 includes a rounded, squared, pointed, or tapered boundary, or any other termination such that regions of rod support housing 26 may temporarily flex to accommodate and seat screw head 18 and locking ring 16, as detailed further below. Relief slots 48 refers to at least two slots spaced either equidistant from each other or at variable distances from each other. Rod support housing 26 is generally tapered outwardly from head capture opening 40 to approximately the termination of relief slots 48, though the tapering may be continuous or in one or more steps, as described in detail below. As shown in FIG. 3, when screw head 18 of pedicle screw 12 is aligned with head capture opening 40 and screw shaft 20 is positioned outside of head capture opening 40, pedicle screw 12 is properly positioned for insertion into and seating within rod support housing 26. Pressure and/or rotation of pedicle screw 12 as it is inserted allows regions of rod support housing 26 between relief slots 48 to flex outwardly to allow screw head 18 to enter head capture opening 40 and pass over gripping ridge 42. Regions of rod support housing 26 between relief slots 48 cease to flex outwardly after screw head 18 is seated within rod support housing 40. The flexing of regions of rod support housing 26 between relief slots 48 does not permit screw head 18 to pass beyond stopping ridge 46.

Referring back to FIG. 4, rod support housing 26 has a locking groove 50 along an exterior surface of the distal end of rod support housing 26 with an outer diameter formed by an outermost edge 52 of locking groove 50. Locking groove 50 is located between two tapered regions on the exterior surface of rod support housing 26, where a first tapered region tapers outward from the centerline of central channel 24 between head capture opening 40 and locking groove 50, and a second tapered region tapers outward from the centerline of central channel 24 between locking groove 50 and approximately the same height along rod support housing 26 as stopping ridge 46. In embodiments not shown, tapering regions may be arranged at different points, at differing angles, or may include more tapering regions than are depicted in FIG. 4. Locking groove 50 serves as a feature corresponding to a locking tab 54 on locking ring 16, such that locking ring 16 may fit over and lock onto rod support housing 26, as detailed below.

Figure 7:
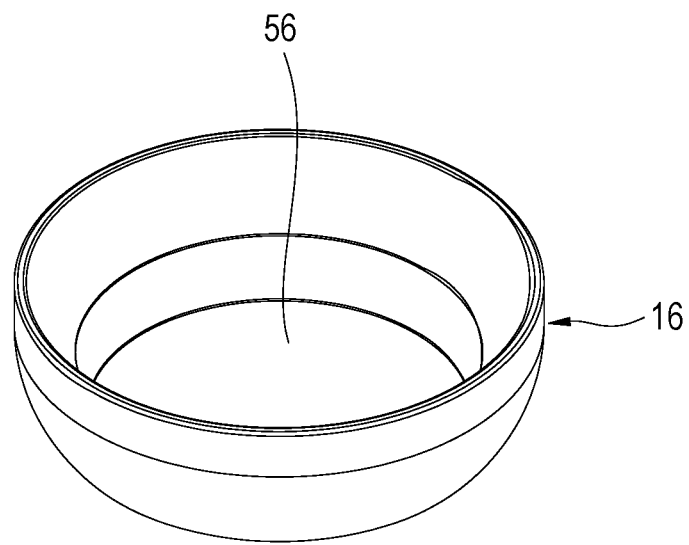
FIG. 7 is perspective view of a locking ring of the pedicle screw system of FIG. 1.
Figure 8:
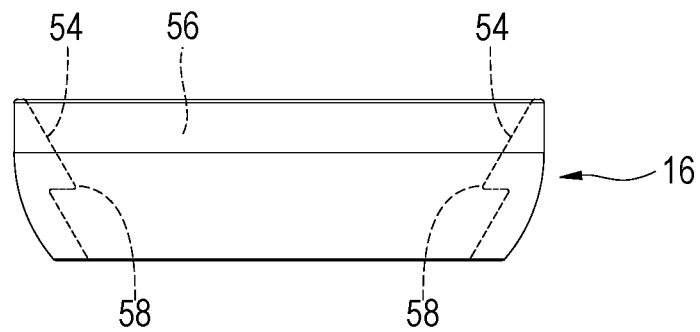
FIG. 8 is an elevational view of the locking ring of the pedicle screw system of FIG. 1.
Figure 9:
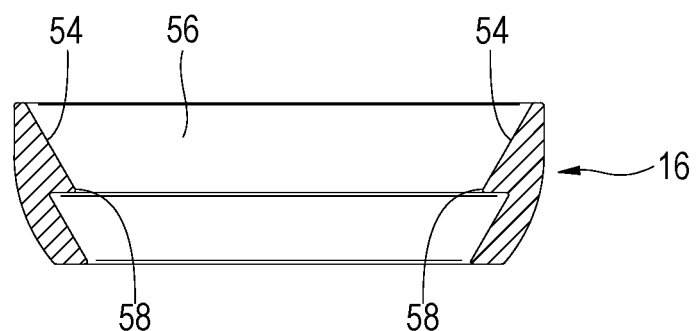
FIG. 9 is a sectional view of the locking ring of the pedicle screw system of FIG. 1.

Now referring to FIGS. 7-9, locking ring 16 is depicted with a central opening 56 extending from a proximal to a distal end of locking ring 16. Central opening 56 has a boundary forming a shape of a circle, or any other shape corresponding to the cross section of the exterior surface of the distal end of rod support housing 26. The exterior surface of locking ring 16 is rounded in FIG. 8, though it may be tapered or parallel to a centerline through central opening 56 in embodiments of the invention that are not depicted. Locking tab 54 is located along and extends from an interior surface of locking ring 16 and has a tab diameter formed by an innermost point 58 of locking tab 54, which is slightly smaller than the outer diameter of locking groove 50. The slightly smaller tab diameter is sufficiently smaller than the outer diameter, such that in a resting state without application of pressure, stress, or rotation, locking ring 16 does not pass over head capture opening 40, outermost edge 52, and into locking groove 50, but also such that with application of pressure, stress, or rotation, head capture opening 40 and outermost edge 52 of locking groove 50 are capable of flexing to accommodate the passage of locking ring 16 into locking groove 50. The interior surfaces of locking ring 16 include two tapered regions, though there may be more than two tapered regions or tapered regions of different lengths and taper angles in embodiments not depicted. In the embodiment shown in FIGS. 8-9, first interior taper region tapers inward from the centerline of central opening 56 between the distal end of locking ring 16 and locking tab 54, and a second interior taper region tapers inward from the centerline of central opening 56 between locking tab 54 and the proximal end of locking ring 16.

Referring to FIG. 3, placing locking ring 16 around screw shaft 20 of inserted pedicle screw 12 and against head capture opening 40 allows proper positioning of locking ring 16 prior to application of pressure and locking of locking ring 16. The proximal end of locking ring 16, which has a larger inner diameter than the distal end of locking ring 16, should be positioned against head capture opening 40. After placement, the pressing of locking ring 16 over head capture opening 40 of rod support housing 26 allows regions of rod support housing 26 between relief slots 48 to flex inwardly to allow locking tab 54 to pass over outermost edge 52 of locking groove 50 and into locking groove 50. For example, the inward flexing of regions of rod support housing 26 decreases a diameter of head capture opening 40 by about 0.016 inches to accommodate the passage of locking ring 16 in one instance. Regions of rod support housing 26 between relief slots 48 cease to flex inwardly after locking tab 54 is seated within locking groove 50. In this configuration, pedicle screw system 10 is assembled and locking ring 16 and pedicle screw 12 are locked to rod support housing 26. After locking of locking ring 16 and pedicle screw 12 to rod support housing 26, movement of screw head 18 over gripping ridge 42 forces locking groove 50 and outermost edge 52 into further contact with locking tab 54 of locking ring 16, such that locking ring 16 prevents the removal of pedicle screw 12 from rod support housing 26.

In a surgical setting, assembled pedicle screw system 10 allows the insertion of pedicle screw 12 and is capable of detaching extension portion 28 from rod support housing 26 at separation notch 30 after screw insertion. Extension portion 28 is separated by a first step of severing connection bridge 38 of cutout 36. The severing results in the forming of at least two panels from material between cutout 36 and longitudinal slot 34. The panels are configured to be bent at separation notch 30, such that bending of the proximal end of the panels outward from the centerline of central channel 24 results in their separation from rod support housing 26, and leave a modular pedicle tulip 60.

Figure 10:
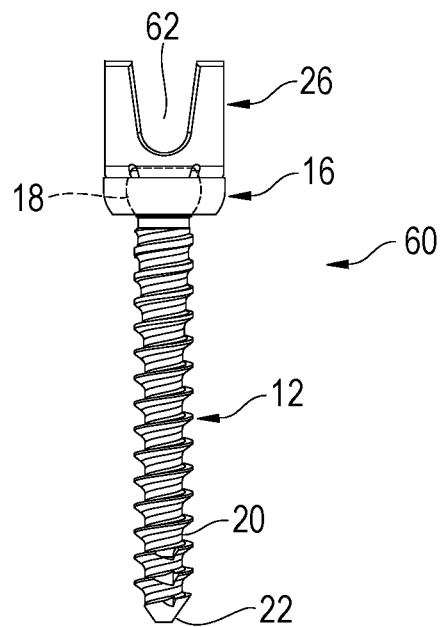
FIG. 10 is an elevational view of a modular pedicle tulip forming a detachable portion of the pedicle screw system of FIG. 1.

Referring to FIG. 10, modular pedicle tulip 60 includes rod support housing 26, central channel 24, and pedicle screw 12 and may also be assembled as described above for pedicle screw system 10, with the exception that extension portion 28 and separation notch 30 are not present. Each modular pedicle tulip 60 includes at least a pair of longitudinal rod slots 62 extending from the proximal end of rod support housing 26 and that is configured to house rods that connect multiple pedicle tulips 60 in a surgical setting. Rod slots 62 terminate in a shape that is rounded, tapered, pointed, squared, or any other boundary shape such that rods may be inserted and held in position in pedicle tulip 60. Additionally, rod slots 62 are the remaining regions of cutout 36 and longitudinal slot 34 in instances where extension portion 28 is removed from rod support housing 26.

Figure 11:
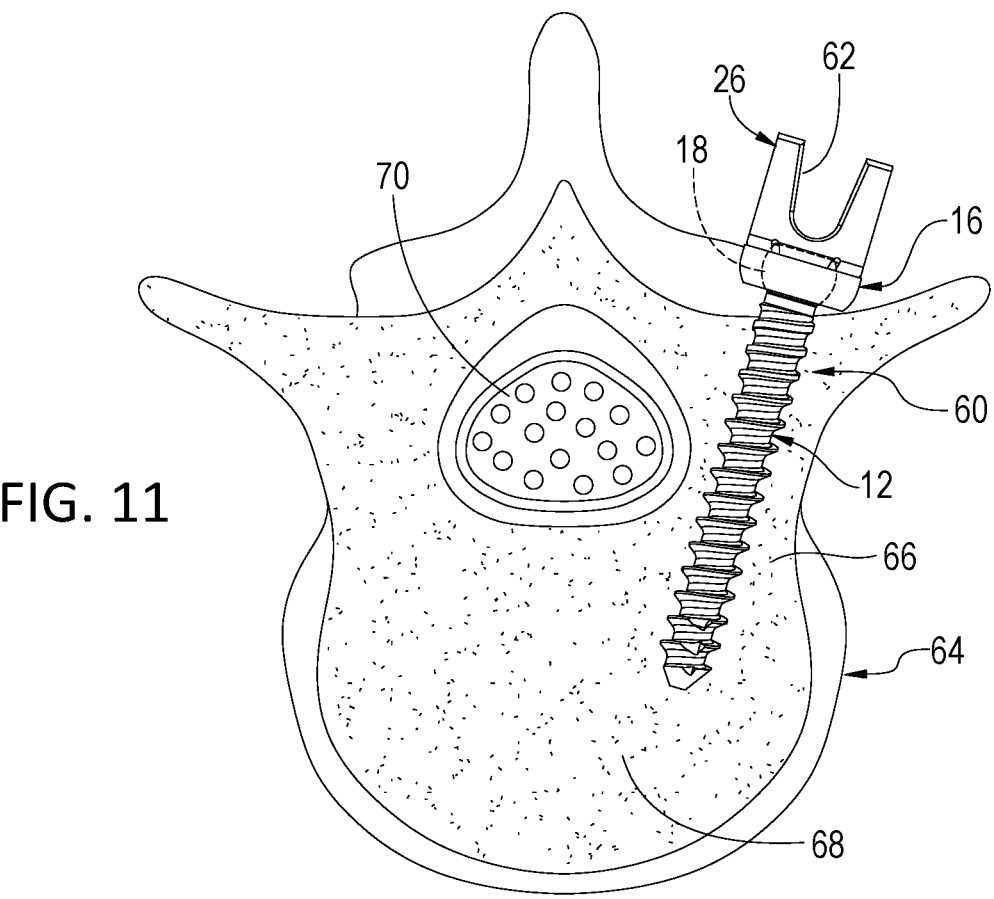
FIG. 11 is a partial sectional view of a vertebra, including vertebral pedicles, illustrating the modular pedicle tulip of the pedicle screw system of FIG. 1 inserted into the vertebra, traversing the pedicle, and entering the vertebral body.

An exemplary insertion location for pedicle screw system 10 in a vertebra is shown in FIG. 11. Specifically, pedicle screw system 10 is inserted into a vertebra 64, traverses a pedicle 66, and enters a vertebral body 68. Care is given during insertion to avoid breaching a vertebral foramen 70 in an effort to avoid vertebral and nerve damage. Pedicle screw systems 10 are generally inserted into multiple vertebrae 64, such that rods connecting modular pedicle tulips 60 stabilize vertebrae 64 and allow spinal fusion of vertebrae 64. Vertebrae 64 for modular pedicle tulip 60 insertion are often located in the lumbar spine, though thoracic or sacral vertebrae may also serve as insertion locations.

Figure 12:
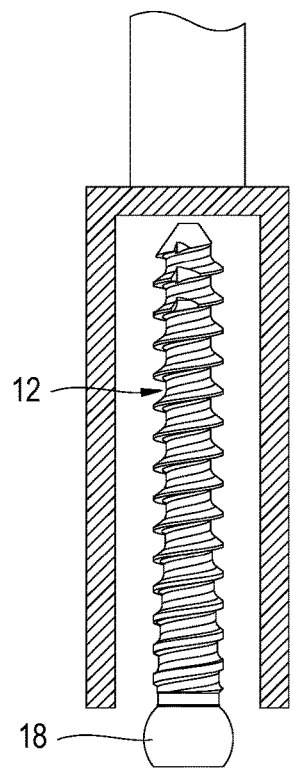
FIG. 12 is an elevational view of a pre-assembled pedicle screw and rod support housing of the pedicle screw system of FIG. 1.
Figure 13:
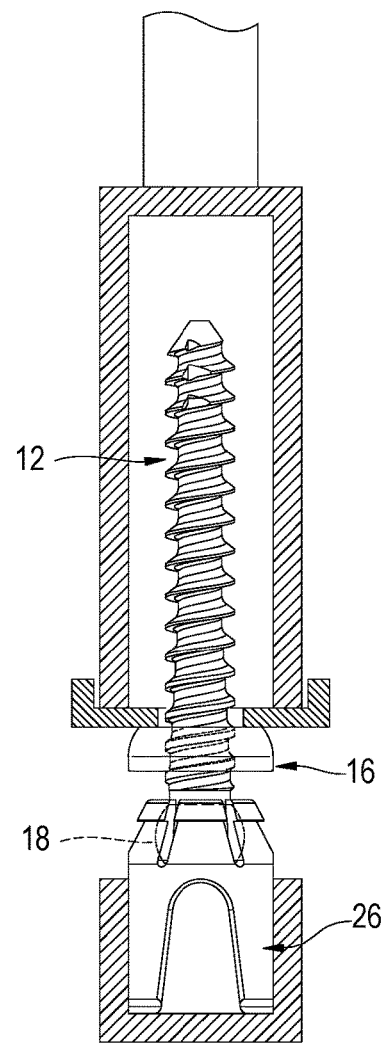
FIG. 13 is an elevational view of the modular pedicle tulip of the pedicle screw system of FIG. 1 with the locking ring positioned for assembly.
Figure 14:
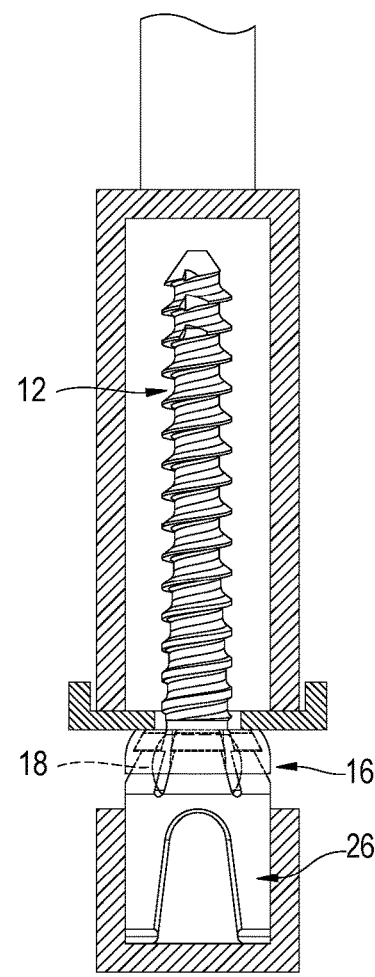
FIG. 14 is an elevational view of the modular pedicle tulip of the pedicle screw system of FIG. 1 with the locking ring assembled.

Pre-assembly of pedicle screw system 10 or modular pedicle tulip 60 is accomplished, by example, in the steps shown in FIGS. 12-14. In a first step, pedicle screw 12 is oriented with screw head 18 aligned with head capture opening 40 of rod support housing 26 and with screw shaft 20 directed away from head capture opening 40. Rod support housing 26 or modular pedicle tower 14 (not depicted) is secured in a base and a hollow bushing or other hollow support structure is fitted over pedicle screw 12, orienting it for insertion. The hollow bushing provides force to push pedicle screw 12 into rod support housing 26 through head capture opening 40 without surpassing stopping ridge 46. An inserted pedicle screw 12 is shown in FIG. 13, with locking ring 16 positioned for assembly. Locking ring 16 is oriented with the semi-spherical exterior region positioned away from rod capture housing 26 and with screw shaft 20 within central opening 56. Between locking ring 16 and the hollow bushing is an alignment plate or other platform capable of applying even pressure to locking ring 16 without applying further pressure to pedicle screw 12. FIG. 14 depicts the assembled modular pedicle tulip 60 as locking ring 16 has been pushed into a locked position on rod support housing 26. In embodiments not depicted where rod support housing 26 is attached to extension portion 28, assembly results in pedicle screw system 10.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

We claim:

1. A pedicle screw system comprising:
   a screw including a screw shaft and a screw head having a major diameter,
   a pedicle tower including a rod support housing including a head capture opening surrounded circumferentially by relief slots at a distal end of the rod support housing, a gripping ridge along an interior surface of the rod support housing, an inner diameter formed by an innermost point of the gripping ridge that is slightly smaller than the major diameter of the screw head, and a locking groove along an exterior surface of a distal end of the rod support housing with an outer diameter formed by an outermost edge of the locking groove, and
   a locking ring including a central opening and a locking tab, wherein the locking tab is located along and extends from an interior surface of the locking ring and wherein a tab diameter formed by an innermost point of the locking tab is slightly smaller than the outer diameter of the locking groove,
   wherein the exterior surface of the distal end of the rod support housing includes (i) a first portion tapering inwardly as the first portion extends distally and (ii) a second portion, distal to the first portion, tapering inwardly as the second portion extends distally, wherein a distal end of the first portion has a diameter that is less than a diameter of a proximal end of the second portion.

2. The system of claim 1 wherein regions of the rod support housing between the relief slots are configured to flex outwardly and the rod support housing is configured to receive the screw head upon pressing the screw head through the head capture opening and over the gripping ridge.

3. The system of claim 2 wherein regions of the rod support housing between the relief slots are configured to flex inwardly and the rod support housing is configured to receive the locking ring upon pressing the locking ring over the head capture opening and engaging the locking tab within the locking groove, such that, when the screw head is seated within the rod support housing and the locking ring is subsequently placed over the rod support housing, regions of the rod support housing between the relief slots are thereafter unable to flex and both the locking ring and the pedicle screw are locked to the rod support housing.

4. The system of claim 1 wherein regions of the rod support housing between the relief slots are configured to flex inwardly and the rod support housing is configured to receive the locking ring upon pressing the locking ring over the head capture opening and engaging the locking tab within the locking groove, such that, when the screw head is seated within the rod support housing and the locking ring is subsequently placed over the rod support housing, regions of the rod support housing between the relief slots are thereafter unable to flex and both the locking ring and the pedicle screw are locked to the rod support housing.

5. The system of claim 1 including a stopping ridge along the interior surface of the rod support housing configured for preventing the pedicle screw from entering a threaded driver region of the pedicle tower.

6. The system of claim 1 wherein the pedicle tower includes a cutout and a longitudinal slot, the cutout extending from a connection bridge at the proximal end of the pedicle tower to the distal end of the pedicle tower and the longitudinal slot extending from the proximal end of the pedicle tower to the distal end of the pedicle tower.

7. The system of claim 1, wherein the interior surface of rod support housing extending between the head capture opening and the gripping ridge is parallel to a longitudinal centerline of a central channel of the pedicle tower.

8. The system of claim 1, wherein the locking groove is formed between the first portion and the second portion.

9. The system of claim 1, wherein the exterior surface of the distal end of the rod support housing includes a third portion extending radially relative to a longitudinal axis of the rod support housing and to and between the distal end of end of the first portion and the proximal end of the second portion.

10. The system of claim 1, wherein an interior surface of the locking ring includes (i) a fourth portion tapering inwardly as the fourth portion extends distally and (ii) a fifth portion, distal to the fourth portion, tapering inwardly as the fifth portion extends distally, wherein a distal end of the fourth portion has a diameter that is less than a diameter of a proximal end of the fifth portion.

11. The system of claim 10, wherein the locking tab is formed between the third portion and the fourth portion.

12. The system of claim 10, wherein the interior surface of the locking ring includes a sixth portion extending radially to and between the distal end of end of the third portion and the proximal end of the fourth portion.

13. A pedicle screw comprising:
a screw including a screw shaft and a screw head,
a pedicle tower including a rod support housing including a head capture opening surrounded circumferentially by relief slots at a distal end of the rod support housing and an exterior surface with a locking groove, wherein the screw head is received within the head capture opening, and
a locking ring having an interior surface with a locking tab, wherein the locking ring surrounds the distal end of the rod support housing and the screw head and the locking tab is received within the locking groove,
wherein an interior surface of the locking ring includes (i) a first surface tapering inwardly as the first surface extends distally and (ii) a second surface, distal to the first surface, tapering inwardly as the second surface extends distally, wherein a distal end of the first surface has a diameter that is less than a diameter of a proximal end of the second.

14. The pedicle screw of claim 13, wherein the locking tab is formed between the first surface and the second surface.

15. The pedicle screw of claim 13, wherein the interior surface of the locking ring includes a third surface extending radially to and between the distal end of end of the first surface and the proximal end of the second surface.

16. The pedicle screw of claim 13, wherein the exterior surface of the distal end of the rod support housing includes (i) a fourth surface tapering inwardly as the fourth surface extends distally and (ii) a fifth surface, distal to the fourth surface, tapering inwardly as the fifth surface extends distally, wherein a distal end of the fourth surface has a diameter that is less than a diameter of a proximal end of the fifth surface.

17. The pedicle screw of claim 16, wherein the locking groove is formed between the fourth surface and the fifth surface.

18. The pedicle screw of claim 13, wherein the interior surface of rod support housing extending between the head capture opening and the gripping ridge is parallel to a longitudinal centerline of a central channel of the pedicle tower.

19. A pedicle screw system comprising:
a screw including a screw shaft and a screw head having a major diameter,
a pedicle tower including a rod support housing including a head capture opening surrounded circumferentially by relief slots at a distal end of the rod support housing, a gripping ridge along an interior surface of the rod support housing, an inner diameter formed by an innermost point of the gripping ridge that is slightly smaller than the major diameter of the screw head, and a locking groove along an exterior surface of a distal end of the rod support housing with an outer diameter formed by an outermost edge of the locking groove, and
a locking ring including a central opening and a locking tab, wherein the locking tab is located along and extends from an interior surface of the locking ring and wherein a tab diameter formed by an innermost point of the locking tab is slightly smaller than the outer diameter of the locking groove,
wherein the interior surface of rod support housing extending between the head capture opening and the gripping ridge is parallel to a longitudinal centerline of a central channel of the pedicle tower.

20. The system of claim 19, wherein the locking groove is located between a first tapered surface and a second tapered surface.

* * * * *